United States Patent
Jeng et al.

(10) Patent No.: US 6,799,346 B2
(45) Date of Patent: Oct. 5, 2004

(54) TOOTHBRUSH WITH OPPOSITELY RECIPROCATING BRUSH HEADS

(75) Inventors: Johnny Jeng, Taipei (TW); Taer Mandry, Kowloon (HK); Whiter Shieh, Taipei (TW)

(73) Assignee: Atico International USA, Inc., Ft. Lauderdale, FL (US)

(*) Notice: Subject to any disclaimer, the term of this patent is extended or adjusted under 35 U.S.C. 154(b) by 88 days.

(21) Appl. No.: 10/040,322

(22) Filed: Jan. 4, 2002

(65) Prior Publication Data

US 2003/0126700 A1 Jul. 10, 2003

(51) Int. Cl.⁷ .............................................. A46B 13/02
(52) U.S. Cl. ............................................ 15/28; 15/22.1
(58) Field of Search ........................... 15/28, 29, 22.1, 15/23, 24

(56) References Cited

U.S. PATENT DOCUMENTS

| | | |
|---|---|---|
| 723,983 A | 3/1903 | Brooke |
| 1,420,388 A | 6/1922 | Schworm |
| 1,620,330 A | 3/1927 | Douglass |
| 2,259,797 A | 10/1941 | Cohen |
| 2,911,660 A | 11/1959 | Klemas et al. |
| 3,195,537 A | 7/1965 | Blasi |
| 3,220,039 A | 11/1965 | Dayton et al. |
| 3,242,516 A * | 3/1966 | Cantor ................. 15/28 |
| 3,775,800 A | 12/1973 | Veneziani |
| 3,848,336 A | 11/1974 | Copeland |
| 3,932,908 A * | 1/1976 | Bitgood et al. ................. 15/28 |
| 4,203,431 A | 5/1980 | Abura et al. |
| 4,827,550 A | 5/1989 | Graham et al. |
| 4,829,218 A | 5/1989 | Bauer |
| 4,914,376 A | 4/1990 | Meyer |
| 4,989,287 A | 2/1991 | Scherer |
| 5,070,567 A | 12/1991 | Holland |
| 5,099,536 A * | 3/1992 | Hirabayashi ................. 15/28 |
| 5,120,225 A | 6/1992 | Amit |
| 5,170,525 A | 12/1992 | Cafaro |
| 5,186,627 A | 2/1993 | Amit et al. |
| 5,274,870 A | 1/1994 | Stollman |
| 5,289,604 A | 3/1994 | Kressner |
| 5,341,534 A | 8/1994 | Serbinski et al. |
| 5,378,153 A | 1/1995 | Giuliani et al. |
| 5,467,495 A | 11/1995 | Boland et al. |
| 5,504,958 A | 4/1996 | Herzog |
| 5,546,674 A | 8/1996 | Lange et al. |
| 5,577,285 A | 11/1996 | Drossler |
| 5,590,434 A | 1/1997 | Imai |
| 5,613,258 A | 3/1997 | Hilfinger et al. |
| 5,652,990 A | 8/1997 | Driesen et al. |
| 5,673,710 A | 10/1997 | Schaefer et al. |
| 5,709,233 A | 1/1998 | Boland et al. |
| 5,732,433 A | 3/1998 | Göcking et al. |
| 5,842,244 A | 12/1998 | Hilfinger et al. |
| 5,850,655 A | 12/1998 | Göcking et al. |
| 5,862,558 A | 1/1999 | Hilfinger et al. |

(List continued on next page.)

FOREIGN PATENT DOCUMENTS

| | | |
|---|---|---|
| DE | 3428860 A1 | 2/1986 |
| DE | 3524586 A1 | 1/1987 |
| DE | 3744630 A1 | 7/1989 |
| DE | 4125168 A1 | 4/1992 |
| DE | 4201873 C1 | 5/1993 |
| EP | 0173150 | 8/1985 |
| FR | 2 587 183 | 9/1985 |
| WO | WO 91/07116 | 5/1991 |
| WO | WO 92/19125 | 11/1992 |

Primary Examiner—Gary K. Graham
(74) Attorney, Agent, or Firm—Gibbons, Del Deo, Dolan, Griffinger & Vecchione

(57) ABSTRACT

An electric toothbrush having a handle which houses a motor and a toothbrush member. The toothbrush member is configured for coupling with the handle. The toothbrush member has a plurality of brushes that rotate in opposite directions to enhance teeth cleaning, plaque removal and gum prophylaxis. Two separate switches are provided, one providing momentary operation and the other continuous.

4 Claims, 2 Drawing Sheets

U.S. PATENT DOCUMENTS

| | | |
|---|---|---|
| 5,867,856 A | 2/1999 | Herzog |
| 5,893,715 A | 4/1999 | Boland et al. |
| 5,927,300 A | 7/1999 | Boland et al. |
| 5,943,723 A | 8/1999 | Hilfinger et al. |
| 5,974,613 A | 11/1999 | Herzog |
| 5,974,615 A | 11/1999 | Schwarz-Hartmann et al. |
| 6,000,083 A | 12/1999 | Blaustein et al. |
| 6,009,589 A | 1/2000 | Driesen et al. |
| 6,021,538 A | 2/2000 | Kressner et al. |
| D425,414 S | 5/2000 | Baker et al. |
| 6,059,106 A | 5/2000 | Baker et al. |
| 6,102,700 A | 8/2000 | Haczek et al. |
| 6,126,008 A | 10/2000 | Cox |
| 6,141,819 A | 11/2000 | Driesen et al. |
| 6,189,693 B1 | 2/2001 | Blaustein et al. |

\* cited by examiner

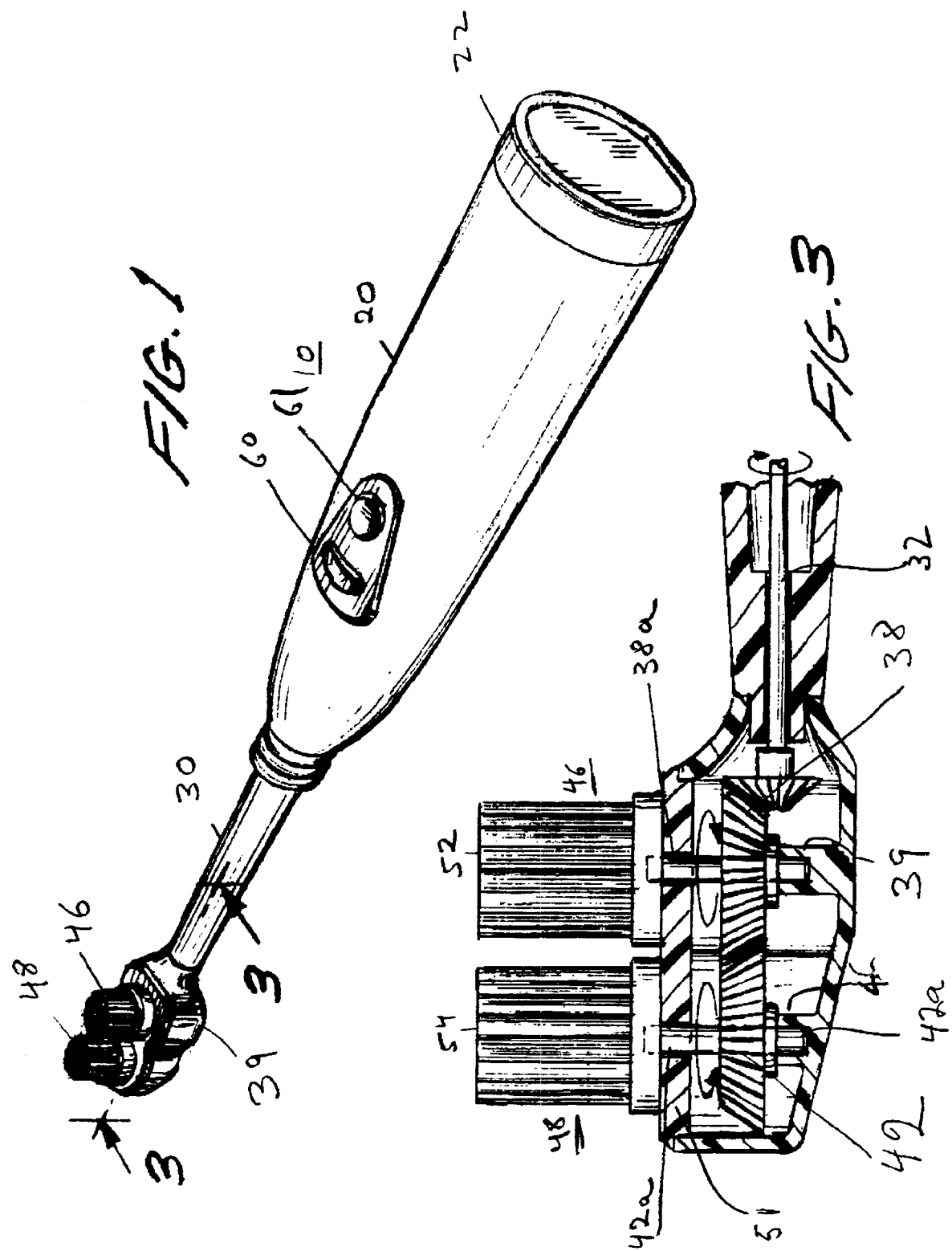

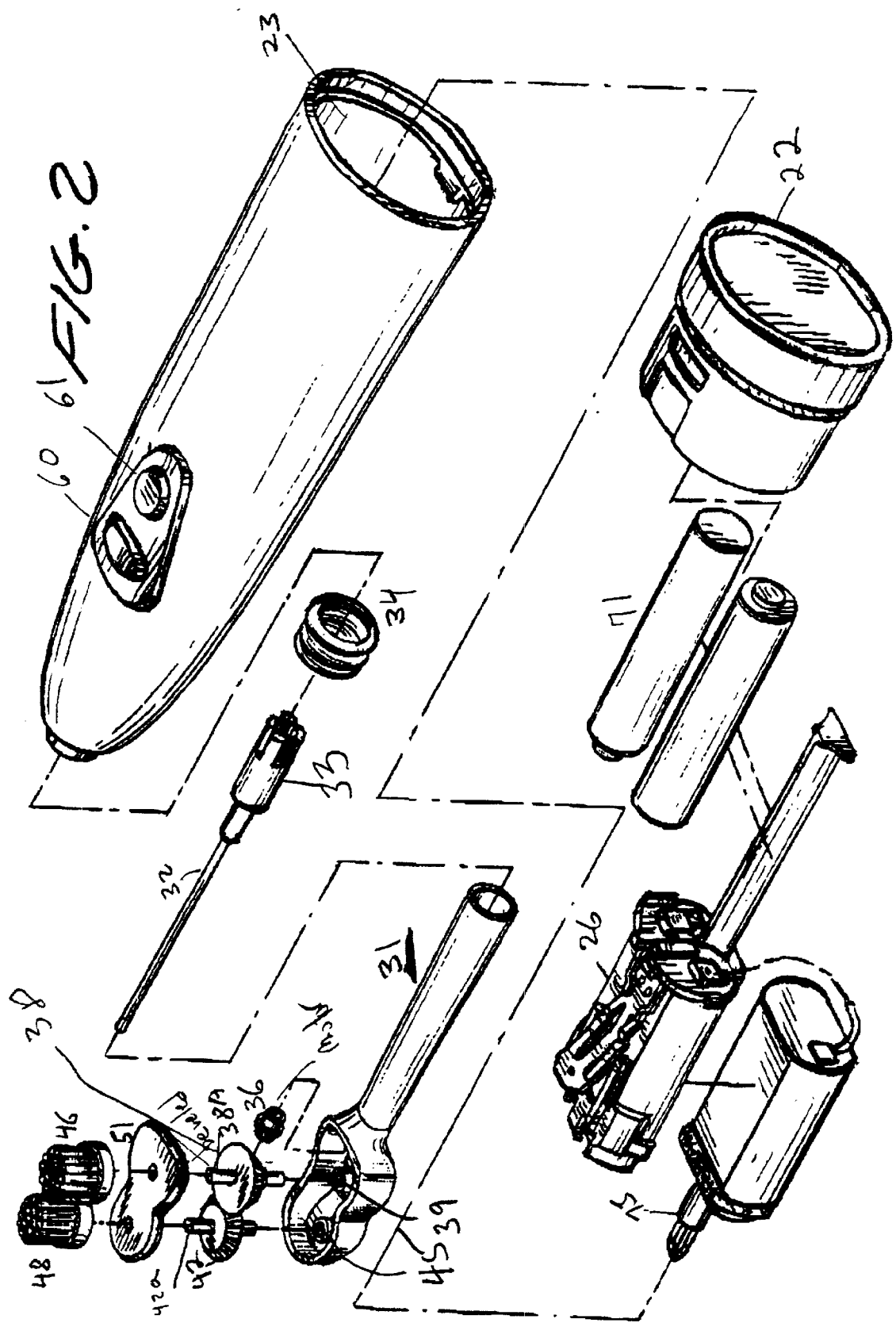

TOOTHBRUSH WITH OPPOSITELY RECIPROCATING BRUSH HEADS

CROSS-REFERENCE TO RELATED PATENT APPLICATIONS

STATEMENT REGARDING FEDERALLY SPONSORED RESEARCH OR DEVELOPMENT

Not Applicable.

BACKGROUND OF THE INVENTION

1. Field of the Invention

This invention pertains to an electric toothbrush, and specifically to an electrical toothbrush having more than one cluster of rotating bristles wherein the clusters rotate in opposite directions relative to each other.

2. Discussion of the Related Art

There have been attempts to enhance toothbrushing and the efficacy of plaque removal from a user's teeth by employing electrical toothbrushes configured with various rotational speeds of the brush sections or by using a specific angle(s) of brush heads.

In addition to the actual cleaning of the teeth and removal of plaque performed by brushing one's teeth with an electric toothbrush, it is also desirable to massage the gums in order to retain their health, a procedure referred to as prophylaxis.

What is needed is an electric toothbrush with an enhanced cleaning operation.

What is also needed is an electric toothbrush that provides improved gum prophylaxis during brushing.

What is further needed is an electric toothbrush with a plurality of brush heads that provide a plurality of brushing directions to yield enhanced teeth cleaning and plaque removal.

What is further needed is an improved electric toothbrush head configured for the above-described needs.

BRIEF SUMMARY OF THE INVENTION

The electric toothbrush of the instant invention is equipped with two brushes that rotate in opposite directions to enhance the efficacy of toothbrushing. By employing two brushes that rotate in opposite directions, the teeth cleaning and removal of plaque is enhanced because the areas that make contact with the toothbrush are cleaned in two directions. Thus, whichever areas and crevices are missed by one brush because the rotation of the brush at the time of cleaning this area did not cover a specific area, can now be contacted by the second brush when it rotates in the opposite direction.

The instant invention also improves prophylaxis of the gums during brushing, because areas that would not be massaged as a result of bushing in one direction are now subject to being massaged by the second brush rotating in an opposite direction. This procedure is further improved if the user switches hands while toothbrushing.

BRIEF DESCRIPTION OF THE DRAWINGS

FIG. 1 is a perspective view of the electric toothbrush of the present invention;

FIG. 2 is an exploded, perspective view of the toothbrush of the present invention showing various parts thereof; and FIG. 3 is a sectional view and taken substantially along the line 3—3 of FIG. 1.

DETAILED DESCRIPTION OF THE INVENTION

The toothbrush of the present invention is described herein with reference to FIGS. 1 through 3. Referring to FIG. 1, the electric toothbrush 10 comprises a handle 20 and a toothbrush member 30. As shown in FIG. 2., the handle defines a housing 23 for housing a motor 26 and a battery power source consisting of batteries 71 for energizing the motor 26. There is also provided a housing for receiving batteries 71 to provide power to the motor, although the batteries 71 are not part of this invention. A handle cover 22 is removably affixed to the handle 20 in order to allow for easy replacement of batteries 71.

Switch 60 turns the motor on and switch 61 turns the motor off.

A motor shaft 75 is operatively connected to the motor 26 such that when the motor 26 is in an ON condition, the motor shaft 75 rotates in response thereto along its longitudinal axis.

A toothbrush member 30 is provided that is connected to the handle 20 by a connector 34 as shown in FIG. 2. The toothbrush member 30 comprises a body 31, a drive shaft 32, a transition gear 36, a first bevel gear 38, a second bevel gear 42, a first brush 46 and a second brush 48. The transition gear attaches to shaft 32. The body 31 of the toothbrush member 30 is configured to house the drive shaft 32 which is configured for coupling via coupling 33 with the motor shaft 75 at a first end such that when the motor shaft 75 rotates, the drive shaft 32 also rotates in response thereto via coupling 33. The drive shaft 32 is coupled to mesh with transition gear 36 at a second end such that when the drive shaft 32 rotates, the transition gear 36 rotates in a plane that is at a substantially right angle to a plane of rotation of the drive shaft 32 (FIG. 3).

The first bevel gear 38 is meshed with the transition gear 36 such that when the transition gear 36 rotates, the first bevel gear 38 rotates in a plane that is at substantially a right angle to the plane of rotation of the transition gear 36 (FIG. 3). A shaft 38a extends through bevel gear 38 with its bottom received in a bearing housing 39. The uppermost portion of shaft 38a extends through a hole in plate 51 to the interior of first brush 46 such that the first brush rotates with shaft 38a. The second bevel gear 42 is meshed with the first bevel gear 38 such that when the first bevel gear 38 rotates, the second bevel gear 42 rotates in an opposite direction.

A second brush 48 is coupled to shaft 42a which rotates with bevel gear 42. The shaft extends 42a through second bevel gear 41 with its bottom portion received in bearing housing 45. Bevel gears 38 and 42 are in mesh with each other. As a result of this arrangement, each of the brushes 46, 48 rotate in opposite directions while the electric toothbrush 10 is in operation. That is, one rotates clockwise while the other rotates counterclockwise.

As shown in FIG. 3, the first brush 46 and second brush 48 may be comprised of a series of tufted bristles 52, 54 arranged in a substantially circular manner so as to facilitate easy maneuverability of the brushes 46, 48 within the oral cavity of a user. In addition, a protective plate 51 to protect against gears 36, 38, 42 from foreign particles such as dust, toothpaste and liquids which they may otherwise contact and compromise the efficacy of the gears 36, 38, 42. Hence, the protective plate 51 preserves and prolongs the life of the electric toothbrush 10.

When the motor 26 operates, it turns motor shaft 75, which in turn rotates the drive shaft 32 via coupling 33. The opposite end of the shaft 32 is secured by coupling 33 to the transition gear 36 to rotate the same. The transition gear 36 has teeth that mesh with the first bevel gear 38 to rotate the same, say, in a clockwise direction. The teeth of the second bevel gear 42 rotates with those of the first bevel gear so that the second bevel gear 42 rotates counterclockwise since the first bevel gear 38 rotates clockwise. The brushes 46, 48 that are attached respectively to shafts of bevel gears 38, 42 rotate in opposite directions relative to each other; i.e. in the same direction as that of the respective bevel gears to which they are attached.

Although the present invention has been described in relation to particular embodiments thereof, many other variations and modifications and other uses may become apparent to those skilled in the art. It is preferred, therefore, that the present invention be limited not by this specific disclosure herein, but only by the appended claims.

What is claimed is:

1. An electric toothbrush comprising:
   (a) a handle defining a housing in which is disposed a battery operated electric motor;
   (b) a motor shaft mounted in the housing along a longitudinal axis, the motor shaft being connected to the battery operated electric motor such that when the battery operated electric motor is in an ON condition, the motor shaft rotates in a direction of motion relative to its longitudinal axis;
   (c) a battery housing situated within the handle housing for receiving at least a battery, an ON switch configured with the housing to effect operation of the electric toothbrush in response to manual pressure applied to the ON switch and an OFF switch configured with the housing to effect termination of the electric toothbrush in response to manual pressure applied to the OFF switch; and
   (d) a toothbrush member comprising:
      1. a body having a first end and a second end, said first end configured to be insertably coupled in said handle, said body housing a drive shaft having a first end and a second end, the first end of the drive shaft being configured for coupling with the motor shaft such that when the motor shaft rotates, the drive shaft rotates in response thereto; said second end of the drive shaft adapted to mesh with a transition gear housed within said body such that the transition gear rotates in a direction of rotation in response to a rotation of said drive shaft;
      2. a first bevel gear having a first central opening, said first bevel gear coupled with said transition gear such that the first bevel gear rotates in a direction of rotation that is at a substantially right angle from a piano of rotation of said transition gear;
      3. a second bevel gear having a second central opening, said second bevel gear meshed with said first bevel gear such that when the first bevel gear rotates, said second bevel gear rotates responsively thereto in a direction that is opposite from the direction of rotation of said first bevel gear;
      4. a first brush shaft having an upper portion and a lower portion, said lower portion extending through the first central opening of the first bevel gear, said lower portion configured for positioning within a bearing housing extending from the second end of the body of the toothbrush member;
      5. a second brush shaft having an upper portion and a lower portion, said lower portion extending through the second central opening of the second bevel gear, said lower portion configured for positioning within the bearing housing;
      6. a first brush arranged with the upper portion of the first brush shaft and a second brush arranged with the upper portion of the second brush shaft such that the first brush and second brush rotate in response to the rotations of the first bevel gear and the second bevel gear via the first shaft and the second shaft; and
      7. a substantially planar protective plate having a first central opening and a second central opening such that the first brush shaft extends through the first central opening of the protective plate and the second brush shaft extends through the second central opening of the protective plate and wherein the protective plate is configured to prevent foreign substances from contacting any of the first bevel gear, the second bevel gear and the transition gear.

2. The electric toothbrush of claim 1 wherein the first bevel gear rotates in a first direction and the second bevel gear rotates in a opposite direction to the first direction.

3. An electric toothbrush comprising:
   (a) a handle defining a housing in which is disposed a motor;
   (b) a motor shaft mounted in the housing along a longitudinal axis, the motor shaft being connected to the motor such that when the motor is in an ON condition, the motor shaft rotates in a direction of motion relative to its longitudinal axis;
   (c) a toothbrush member having:
      1. a body configured to be insertably coupled in said handle, said body housing a drive shaft having a first end and a second end, the first end being configured for coupling with the motor shaft such that when the motor shaft rotates, the drive shaft rotates in response thereto; the second end of the drive shaft adapted to mesh with a transition gear housed within said body such that the transition gear rotates in a direction of rotation in response to a rotation of said second drive shaft;
      2. a first gear configured with said transition gear such that the first gear rotates in a direction of rotation that is at a substantially right angle to a plane of direction of rotation of said transition gear;
      3. a second gear meshed with said first gear such that when the first gear rotates, said second gear rotates responsively thereto in a direction that is opposite from the direction of rotation of said first gear;
      4. a first brush arranged with said first gear and a second brush arranged with said second gear such that the first brush and second brush rotate in response to the rotations of the first gear and the second gear;
      5. a protective plate configured and arranged to prevent foreign substances from contacting any of the first gear, the second gear and the transition gear, the protective plate being interposed between the first brush and the first gear and between the second brush and the second gear and mated to a surface of the body; and
   first and second brush shafts, each distinct from said first and second gears, the protective plate having openings through which extend the first and second brush shaft, the first brush shaft extending from tie first brush and operatively joining the first brush to the first gear, the second brush shaft extending from the second brush and operatively joining the second brush to the second gear.

4. An toothbrush member for use with an electric toothbrush comprising:

1. a body configured for coupling with an electric toothbrush handle, said body housing a drive shaft having a first end and a second end, the first end being configured for coupling with a driving assembly substantially located within the handle such that when the drive assembly rotates, the drive shaft rotates in response thereto; said second end of the drive shaft configured to mesh with a transition gear housed within the body such that the transition gear rotates in a direction response to a rotation of the drive shaft;
2. a first gear configured with the transition gear such that the first gear rotates in a plane that is at a substantially at a right angle from a plane of rotation of said transition gear;
3. a second gear meshed with the first gear such that when the first gear rotates, said second gear rotates responsively thereto in a direction that is opposite from the direction of rotation of said first gear;
4. a first brush arranged with said first gear and a second brush arranged with said second gear such that the first brush and second brush rotate in response to the rotations of the first gear and the second gear;
5. a protective plate configured and arranged to prevent foreign substances from contacting any of the first gear, the second gear and the transition gear, the protective plate being interposed between the first brush and the first gear and between the second brush and the second gear and mated to a surface of the body; and first and second brush shafts, each distinct from said first and second gears, the protective plate having openings through which extend the first and second brush shaft, the first brush shaft extending from the first brush and operatively joining the first brush to the first gear, the second brush shaft extending from the second brush and operatively joining the second brush to the second gear.

* * * * *